US007312378B2

(12) United States Patent
Hannah et al.

(10) Patent No.: US 7,312,378 B2
(45) Date of Patent: *Dec. 25, 2007

(54) NUCLEIC ACIDS ENCODING HEAT STABLE MUTANTS OF PLANT ADP-GLUCOSE PYROPHOSPHORYLASE

(75) Inventors: L. Curtis Hannah, Gainesville, FL (US); Thomas W. Greene, Zionsville, IN (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 61 days.

This patent is subject to a terminal disclaimer.

(21) Appl. No.: 10/970,230

(22) Filed: Oct. 20, 2004

(65) Prior Publication Data

US 2005/0120413 A1 Jun. 2, 2005

Related U.S. Application Data

(63) Continuation of application No. 10/079,478, filed on Feb. 19, 2002, now Pat. No. 6,809,235, which is a continuation-in-part of application No. 09/312,433, filed on May 14, 1999, now Pat. No. 6,403,863, which is a continuation-in-part of application No. 08/972,545, filed on Nov. 18, 1997, now Pat. No. 6,069,300, said application No. 08/972,545.

(60) Provisional application No. 60/031,045, filed on Nov. 18, 1996, provisional application No. 60/085,460, filed on May 14, 1998.

(51) Int. Cl.
*A01N 5/00* (2006.01)
*A01N 5/10* (2006.01)
*C12N 15/82* (2006.01)
*C12N 15/52* (2006.01)

(52) U.S. Cl. ............... 800/298; 536/23.2; 800/289
(58) Field of Classification Search ............... None
See application file for complete search history.

(56) References Cited

U.S. PATENT DOCUMENTS 6,013,861 A 1/2000 Bird et al. .................. 800/284
6,069,300 A 5/2000 Hannah et al. ............. 800/284

FOREIGN PATENT DOCUMENTS

| WO | 9409144 | 4/1994 |
| WO | 9411520 | 5/1994 |
| WO | 9424292 | 10/1994 |
| WO | 9534660 | 12/1995 |
| WO | 9822601 | 5/1998 |
| WO | WO 02/072784 A2 | 9/2002 |

OTHER PUBLICATIONS

Anderson, et al. (1989) "The Encoded Primary Sequence of a Rice Seed ADP-glucose Pyrophosphorylase Subunit and its Homology to the Bacterial Enzyme" J. Biological Chemistry 264(21):12238-12242.

Anderson et al. (1991) "Molecular characterization of the gene encoding a rice endosperm-specific ADPglucose pyrophosphorylase subunit and its developmental pattern of transcription" Gene 97:199-205.

Badu-Apraku, B., R.B. Hunter, M. Tollenaar (1983) "Effect Of Temperature During Grain Filling On Whole Plant And Grain Yield In Maize (*Zea mays* L.)" Can. J. Plant Sci. 63:357-363.

Ballicora et al. (1995) "Adenosine 5'-Diphosphate-Glucose Pyrophosphorylase from Potato Tuber" Plant Physiol. 109:245-251.

Chang, Jen-Hu (1981) "Corn Yield In Relation To Photoperiod, Night Temperature, And Solar Radiation" Agricultural Meteorology 24:253-262.

Charng, Y.Y., Iglesias, A.A., Preiss, J. (1994) "Structure-Function Relationships of Cyanobacterial ADP-glucose Pyrophosphorylase" J. Biol. Chem. 269(39):24107-24113.

Cheikh, N. and R.J. Jones (1995) "Heat stress effects on sink activity of developing maize kernels grown in vitro" Physiologia Plantarium 95:59-66.

Conroy, J.P., S. Seneweera, A.S. Basra, G. Rogers, B. Nissen-Wooller (1994) "Influence of Rising Atmospheric $CO_2$ Concentrations and Temperature on Growth Yield and Grain Quality of Cereal Crops" Aust. J. Plant Physiol. 21:741-758.

Copeland, Les, Jack Preiss (1981) "Purification of Spinach Leaf ADPglucose Pyrophosphorylase" Plant Physiol. 68:996-1001.

Denyer, K., C.M. Hylton, A.M. Smith (1994) "The Effect of High Temperature on Starch Synthesis and the Activity of Starch Synthase" Aust. J. Plant Physiol. 21:783-789.

Dickinson, David B., Jack Preiss (1969) "Presence of ADP-Glucose Pyrophosphorylase in Shrunken-2 and Brittle-2 Mutants of Maize Endosperm" Plant Physiol. 44:1058-1062.

Duke, Edwin R., Douglas C. Doehlert (1996) "Effects Of Heat Stress On Enzyme Activities And Transcript Levels in Developing Maize Kernels Grown In Culture" Environmental and Experimental Botany 36(2):199-208.

Giroux, Michael J. et al. (1996) "A single gene mutation that increases maize seed weight" Proc. Natl. Acad. Sci. USA 93:5824-5829.

Greene, Thomas W. et al. (1996) "Mutagenesis of the potato ADPglucose pyrophosphorylase and characterization of an allosteric mutant defective in 3-phosphoglycerate activation" Proc. Natl Acad. Sci. USA 93:1509-1513.

(Continued)

Primary Examiner—Anne Kubelik
(74) Attorney, Agent, or Firm—Saliwanchik, Lloyd & Saliwanchik

(57) ABSTRACT

The subject invention pertains to novel mutant polynucleotide molecules that encode enzymes that have increased heat stability. These polynucleotides, when expressed in plants, result in increased yield in plants grown under conditions of heat stress. The polynucleotide molecules of the subject invention encode maize endosperm ADP glucose pyrophosphorylase (AGP) and soluble starch synthase (SSS) enzyme activities. Plants and plant tissue bred to contain, or transformed with, the mutant polynucleotides, and expressing the polypeptides encoded by the polynucleotides, are also contemplated by the present invention. The subject invention also concerns methods for isolating polynucleotides and polypeptides contemplated within the scope of the invention. Methods for increasing yield in plants grown under conditions of heat stress are also provided.

21 Claims, 5 Drawing Sheets

OTHER PUBLICATIONS

Greene, Thomas W., Ronald L. Woodbury, Thomas W. Okita (1996) "Aspartic Acid 413 Is Important for the Normal Allosteric Functioning of ADP-Glucose Pyrophosphorylase" Plant Physiol. 112:1315-1320.

Hannah, L. Curtis, Oliver E. Nelson, Jr. (1975) "Characterization of Adenosine Diphosphate Glucose Pyrophosphorylases from Developing Maize Seeds" Plant Physiol. 55:297-302.

Hannah, L. Curtis (1997) "Starch Synthesis in the Maize Seed" In: Cellular and Molecular Biology of Plant Seed Development, B.A. Larkins and I.K. Vasil (eds.), Kluwer Academic Publishers, printed in the Netherlands, p. 375-405.

Hannah, L.C., O.E. Nelson, Jr. (1976) "Characterization of ADP-Glucose Pyrophosphorylase from Shrunken-2 and Brittle-2 Mutants of Maize" Biochemical Genetics 14(7/8):547-560.

Hannah, L.C., D.M. Tuschall, R.J. Mans (1980) "Multiple Forms Of Maize Endosperm ADP-Glucose Pyrophosphorylase And Their Control By Shrunken-2 and Brittle-2" Genetics 95:961-970.

Hawker, J.S., C.F. Jenner (1993) "High Temperature Affects the Activity of Enzymes in the Committed Pathway of Starch Synthesis in Developing Wheat Endosperm" Aust. J. Plant Physiol. 20:197-209.

Iglesias et al. (1993) "Expression of the Potato Tuber ADP-glucose Pyrophosphorylase in Escherichia coli" J. of Biological Chemistry 268(2):1081-1086.

Jenner, C.F. (1994) "Starch Synthesis in the Kernel of Wheat Under High Temperature Conditions" Aust. J. Plant Physiol. 21:791-806.

Jenner, C.F., K. Denyer, J. Guerin (1995) "Thermal Characteristics of Soluble Starch Synthase from Wheat Endosperm" Aust. J. Plant Physiol. 22:703-709.

Jones, R.J., B.G. Gengenbach, V.B. Cardwell (1981) "Temperature Effects On In Vitro Kernel Development of Maize" Crop Science 21:761-766.

Jones, R.J., S. Ouattar, R.K. Crookston (1984) "Thermal Environment During Endosperm Cell Division And Grain Filling in Maize: Effects On Kernel Growth And Development In Vitro" Crop Science 24:133-137.

Keeling, P.L., P.J. Bacon, D.C. Holt (1993) "Elevated temperature reduces starch deposition in wheat endosperm by reducing the activity of soluble starch synthase" Planta 191:342-348.

Lafta, A.M., Lorenzen, J.H. (1995) "Effect of High Temperature on Plant Growth and Carbohydrate Metabolism in Potato" Plant Physiology 109:637-643.

Lin, Tsan-Piao, Timothy Caspar, Chris R. Somerville, Jack Preiss (1988) "A Starch Deficient Mutant of Arabidopsis thaliana with Low ADPglucose Pyrophosphorylase Activity Lacks One of the Two Subunits of the Enzyme" Plant Physiol. 88:1175-1181.

Morell, Matthew, Mark Bloom, Jack Preiss (1988) "Affinity Labeling of the Allosteric Activator Site(s) of Spinach Leaf ADP-glucose Pyrophosphorylase" J. Biological Chemistry 263(2):633-637.

Nakata, Paul A., Thomas W. Greene, Joseph M. Anderson, Brian J. Smith-White, Thomas W. Okita, Jack Preiss (1991) "Comparison of the primary sequences of two potato tuber ADP-glucose pyrophosphorylase subunits" Plant Molecular Biology 17:1089-1093.

Okita, Thomas W., Paul A. Nakata, Joseph M. Anderson, Joseph Sowokinos, Matthew Morell, Jack Preiss (1990) "The Subunit Structure of Potato Tuber ADPglucose Pyrophosphorylase" Plant Physiol. 93:785-790.

Okita et al. (1996) "Engineering Plant Starches by the Generation of Modified Plant Biosynthetic Enzymes" In: Engineering Crops for Industrial End Uses, Shewry, P.R., Napier, J.A., and Davis, P., eds., Portland Press Ltd., London, pp. 1-18.

Olive, M.R., R.J. Ellis, W.W. Schuch (1989) "Isolation and nucleotide sequences of cDNA clones encoding ADP-glucose pyrophosphorylase polypeptides from wheat leaf and endosperm" J. Molecular Biology 12:525-538.

Ou-Lee, Tsai-Mei, Tim Lloyd Setter (1985) "Effect of Increased Temperature in Apical Regions of Maize Ears on Starch-Synthesis Enzymes and Accumulation of Sugars and Starch" Plant Physiol. 79:852-855.

Preiss, J. and T. Romeo (1994) "Molecular Biology and Regulatory Aspects of Glycogen Biosynthesis in Bacteria" Progress in Nuc. Acid Res. and Mol Biol. 47:299-329.

Preiss, J. and M. Sivak (1996) "Starch synthesis in sinks and sources" In: Photoassimilate distribution in plants and crops: source-sink relationships, Zamski, E., ed., Marcil Dekker Inc. pp. 139-168.

Rijven, A.H.G.C. (1986) "Heat Inactivation of Starch Synthase in Wheat Endosperm Tissue" Plant Physiol. 81:448-453.

Shaw, Janine R. and L. Curtis Hannah (1992) "Genomic Nucleotide Sequence of a Wild-Type Shrunken-2 Allele of Zea mays" Plant Physiol. 98:1214-1216.

Singletary, G.W., R. Banisadr, P.L. Keeling (1993) "Decreased Starch Synthesis In Heat Stressed Maize Kernels Results From Reduced ADPG-Pyrophosphorylase And Starch Synthase Activities" Plant Physiol. 102:6(suppl) abstract.

Tsai, C.Y., O.E. Nelson, Jr. (1966) "Starch-Deficient Maize Mutant Lacking Adenosine Diphosphate Glucose Pyrophosphorylase Activity" Science 151:341-343.

Greene, Thomas W. et al. (1998) "Enhanced stability of maize endosperm ADP-glucose pyrophosphorylase is gained through mutants that alter subunit interactions" Proc. Natl. Acad. Sci. USA 95:13342-13347.

Kim, C.H. et al. (1998) "Heat-resistant ADP-glucose pyrophosphorylase produced from Thermas caldophilus sp." Korea Adv. Inst. Sci & Technology XP-002127965 (abstract only).

Laughlin, Mary J. et al. (1998) "N- and C-terminal peptide sequences are essential for enzyme assembly, allosteric, and/or catalytic properties of ADP-glucose pyrophosphorylase" The Plant Journal 14(2):159-168.

Bae, M.M., M. Giroux, L. Hannah (1990) "Cloning And Characterization Of The Brittle-2 Gene Of Maize" Maydica 35:317-322.

Bhave, Mrinal R., Susan Lawrence, Carolyn Barton, L. Curtis Hannah (1990) "Identification and Molecular Characterization of Shrunken-2 cDNA Clones of Maize" The Plant Cell 2:581-588.

Müller-Röber et al. (1990) "One of two different ADP-glucose pyrophosphorylase genes from potato responds strongly to elevated levels of sucrose" Mol Gen Genet 224:136-146.

Singletary, George W., Roshie Banisadr, Peter L. Keeling (1994) "Heat Stress During Grain Filling in Maize: Effects on Carbohydrate Storage and Metabolism" Aust. J. Plant Physiol. 21:829-841.

Sowokinos, Joseph R., Jack Preiss (1982) "Pyrophosphorylases in Solanum tuberosum" Plant Physiol. 69:1459-1466.

Stark, David M., Kurt P. Timmerman, Gerard F. Barry, Jack Preiss, Ganesh M. Kishore (1992) "Regulation of the Amount of Starch in Plant Tissues by ADP Glucose Pyrophosphorylase" Science 258:287-292.

Thompson, Louis M. (1975) "Weather Variability, Climatic Change, and Grain Production" Science 188:535-541.

Thompson, Louis M. (1986) "Climatic Change, Weather Variability, and Corn Production" Agron. J. 78:649-653.

Tollenaar, M., T.W. Bruulsema (1988) "Effects Of Temperature On Rate And Duration Of Kernal Dry Matter Accumulation Of Maize" Can. J. Plant Sci. 68:935-940.

Suzuki, David T. et al. (1989) "Mechanisms of Genetic Change 1: Gene Mutation" In An Introduction to Genetic Analysis, 4th edition, W. H. Freeman and Company, New York, pp. 476-499.

Smith-White, Brian J. et al. (1992) "Comparison of Proteins of ADP-Glucose Pyrophosphorylase from Diverse Sources" J. Mol. Evol. 34:449-464.

Sweetlove, L. J. et al. (1996) "Starch Metabolism in Tubers of Transgenic Potato (Solanum tuberosum) with Increased ADPglucose Pyrophosphorylase" Biochem. J. 320:493-498.

Jensen, L. G. et al. (1996) "Transgenic Barley Expressing a Protein-Engineered, Thermostable (1,3-1,4)-β-Glucanase During Germination" Proc. Natl. Acad. Sci. USA 93:3487-3491.

Greene, Thomas W. et al. (1998) "Generation of Up-regulated Allosteric Variants of Potato ADP-glucose Pyrophosphorylase by Reversion Genetics" Proc. Natl. Acad. Sci. USA 95:10322-10327.

Lazar, E. et al. (1998) "Transforming Growth Factor α: Mutation of Aspartic Acid 47 and Leucine 48 Results in Different Biological Activities" *Molecular and Cellular Biology* 8:1247-1252.

Broun, P. et al. (1998) "Catalytic Plasticity of Fatty Acid Modification Enzymes Underlying Chemical Diversity of Plant Lipids" *Science* 282:1315-1317.

Villand, P. et al. (1992) "ADP-glucose Pyrophosphorylase Large Subunit from Barley Endosperm" *Plant Mol. Biol.*, Accession No. P30524.

Bowie, James U. et al. (1990) "Deciphering the Message in Protein Sequences: Tolerance to Amino Acid Substitutions" *Science* 247:1306-1310.

Ainsworth, C. et al. (1995) "Adenosine Diphosphate Glucose Pyrophosphorylase Genes in Wheat: Differential Expression and Gene Mapping" *Planta*, Accession No. S60572.

Satozawa, T. et al. (1995), Accession No. T02965.

Bhave, M. R. et al. (1990) "Identification and Molecular Characterization of shrunken-2 cDNA Clones of Maize" *Plant Cell*, Accession No. P55241.

|          | Y |   |   |   |
|----------|---|---|---|---|
| HS 33    | LHDFGSEILPRA | VLDH | SVQACI | FTG | YWEDVGTI |
| maize LS | LHDFGSEILPRA | LHDH | NVQAYV | FTD | YWEDIGTI |
| wheat LS | LHDFGSEILPRA | LHDH | NVQAYV | FTD | YWEDIGTI |
| barley LS| LHDFGSEILPA  | AIDD | YNVQAYI | FKD | YWEDIGTI |
| potato LS| SNDFGSEILPA  |      |         |     |          |

Figure 2

|            |   |   |   |   |   |   |   |   |   |   |   |   |   |   |   |   |   |   |   |   |   |   |   |   |   |
|------------|---|---|---|---|---|---|---|---|---|---|---|---|---|---|---|---|---|---|---|---|---|---|---|---|---|
| HS 40      | A | G | K | V | P | I | G | I |   |   | I |   | R | N | T | K | I | R | N | C | I | I | D | M | N | A | R | I | G |
| maize LS   |   | E | G | K | V | P | I | G | V | G |   | E | N | T | K | I | S | N | C | I | I | D | M | N | A | R | I | G |
| wheat LS   |   | E | G | K | V | P | I | G | V | G |   | E | N | T | K | I | S | N | C | I | I | D | M | N | A | R | I | G |
| barley LS  |   | E | G | K | V | P | I | G | I | G |   | E | N | T | K | I | R | K | C | I | I | D | M | N | A | R | I | G |
| potato LS  |   |   |   |   |   |   |   |   |   |   |   |   |   |   |   |   | I | K | D | A | I | I | D | K | N | A | K |   |   |
| spinach LS |   |   |   |   |   |   |   |   |   |   |   |   |   |   |   |   |   | I | K | D | A | I | I | D | K | N | A | R |   |

Figure 3

```
                           #426
TS48                         F
Maize LS    C S R V S S G C E L K D S V M M G A D I
Wheat LS    R S R L N S G S E L K N A M M M G A D S
Barley LS   R S R L N S G S E L K N A M M M G A D S
Rice LS     S S R V S S G C E L K . . . . . . . I
            . S R . S S G . E L K . . . m m g a d .
```

Figure 4A

```
                        #324
TS60                      K
Maize LS    D F G S E I L P R A V L D H S V Q . A C I F T G Y
Wheat LS    D F G S E I L P R A L H D H N V Q . A Y V F T D Y
Barley LS   D F G S E I L P R A L H D H N V Q . A Y V F T D Y
Rice LS     D F G S E I L P R A L L E H N V K V A C V F T E Y
            D F G S E I L P R A l . d H n V q . A . v F T . Y

#359
TS60                                    V
Maize LS    E D V G T I K S F F D A N L A L T E Q P S K F D F
Wheat LS    E D I G T I R S F F D A N M A L C E Q P P K F E F
Barley LS   E D I G T I R S F F D A N M A L C E Q P P K F E F
Rice LS     E D I G T I K S F F D A N L A L T E Q P P K F E F
            E D i G T I   S F F D A N . A L . E Q P p K F e F
```

Figure 4B

```
           #177
RTS48-2     V
Maize LS    T Q M P E E P A G W F Q G T A D S I R K
Wheat LS    T Q M P G E A A G W F R G T A D A V R K
Barley LS   T Q M P G E A A G W F R G T A D A V R K
Rice LS     T Q M P D E P A G W F Q G T A D A I R K
            T Q M P . E . A G W F . G T A D a . R K
```

Figure 5A

```
            #396
RTS60-1      V
Maize LS    D K C K . . M K Y A F I S D G C L L R E
Wheat LS    D K C R . . I K E A I I S H G C F L R E
Barley LS   D K C R . . I K E A I I S H G C F L R E
Rice LS     D K C K C K I K D A I I S D G C S F S E
            D K C . . . i K . A i I S . G C . f r E
```

Figure 5B

SEQUENCE LISTING

<160> NUMBER OF SEQ ID NOS: 36

<210> SEQ ID NO 1
<211> LENGTH: 33
<212> TYPE: PRT
<213> ORGANISM: HS33 Mutant of Zea mays

<400> SEQUENCE: 1

Leu His Asp Phe Gly Ser Glu Ile Leu Pro Arg Ala Val Leu Asp Tyr
1               5                   10                  15

Ser Val Gln Ala Cys Ile Phe Thr Gly Tyr Trp Glu Asp Val Gly Thr
            20                  25                  30

Ile

<210> SEQ ID NO 2
<211> LENGTH: 33
<212> TYPE: PRT
<213> ORGANISM: Zea mays

<400> SEQUENCE: 2

Leu His Asp Phe Gly Ser Glu Ile Leu Pro Arg Ala Val Leu Asp His
1               5                   10                  15

```
Ser Val Gln Ala Cys Ile Phe Thr Gly Tyr Trp Glu Asp Val Gly Thr
            20                  25                  30

Ile

<210> SEQ ID NO 3
<211> LENGTH: 33
<212> TYPE: PRT
<213> ORGANISM: Triticum aestivum

<400> SEQUENCE: 3

Leu His Asp Phe Gly Ser Glu Ile Leu Pro Arg Ala Leu His Asp His
 1               5                  10                  15

Asn Val Gln Ala Tyr Val Phe Thr Asp Tyr Trp Glu Asp Ile Gly Thr
            20                  25                  30

Ile

<210> SEQ ID NO 4
<211> LENGTH: 33
<212> TYPE: PRT
<213> ORGANISM: Hordeum vulgare

<400> SEQUENCE: 4

Leu His Asp Phe Gly Ser Glu Ile Leu Pro Arg Ala Leu His Asp His
 1               5                  10                  15

Asn Val Gln Ala Tyr Val Phe Thr Asp Tyr Trp Glu Asp Ile Gly Thr
            20                  25                  30

Ile

<210> SEQ ID NO 5
<211> LENGTH: 33
<212> TYPE: PRT
<213> ORGANISM: Solanum tuberosum

<400> SEQUENCE: 5

Ser Asn Asp Phe Gly Ser Glu Ile Leu Pro Ala Ala Ile Asp Asp Tyr
 1               5                  10                  15

Asn Val Gln Ala Tyr Ile Phe Lys Asp Tyr Trp Glu Asp Ile Gly Thr
            20                  25                  30

Ile

<210> SEQ ID NO 6
<211> LENGTH: 26
<212> TYPE: PRT
<213> ORGANISM: HS40 Mutant of Zea mays

<400> SEQUENCE: 6

Ala Gly Lys Val Pro Ile Gly Ile Gly Arg Asn Ile Lys Ile Arg Asn
 1               5                  10                  15

Cys Ile Ile Asp Met Asn Ala Arg Ile Gly
            20                  25

<210> SEQ ID NO 7
<211> LENGTH: 26
<212> TYPE: PRT
<213> ORGANISM: Zea mays
```

```
<400> SEQUENCE: 7

Ala Gly Lys Val Pro Ile Gly Ile Gly Arg Asn Thr Lys Ile Arg Asn
 1               5                  10                  15

Cys Ile Ile Asp Met Asn Ala Arg Ile Gly
            20                  25

<210> SEQ ID NO 8
<211> LENGTH: 26
<212> TYPE: PRT
<213> ORGANISM: Triticum aestivum

<400> SEQUENCE: 8

Glu Gly Lys Val Pro Ile Gly Val Gly Glu Asn Thr Lys Ile Ser Asn
 1               5                  10                  15

Cys Ile Ile Asp Met Asn Ala Arg Ile Gly
            20                  25

<210> SEQ ID NO 9
<211> LENGTH: 26
<212> TYPE: PRT
<213> ORGANISM: Hordeum vulgare

<400> SEQUENCE: 9

Glu Gly Lys Val Pro Ile Gly Val Gly Glu Asn Thr Lys Ile Ser Asn
 1               5                  10                  15

Cys Ile Ile Asp Met Asn Ala Arg Ile Gly
            20                  25

<210> SEQ ID NO 10
<211> LENGTH: 26
<212> TYPE: PRT
<213> ORGANISM: Solanum tuberosum

<400> SEQUENCE: 10

Glu Gly Lys Val Pro Ile Gly Ile Gly Glu Asn Thr Lys Ile Arg Lys
 1               5                  10                  15

Cys Ile Ile Asp Lys Asn Ala Lys Ile Gly
            20                  25

<210> SEQ ID NO 11
<211> LENGTH: 11
<212> TYPE: PRT
<213> ORGANISM: Spinicia oleracea

<400> SEQUENCE: 11

Ile Lys Asp Ala Ile Ile Asp Lys Asn Ala Arg
 1               5                  10

<210> SEQ ID NO 12
<211> LENGTH: 20
<212> TYPE: PRT
<213> ORGANISM: TS48 Mutant of Zea mays

<400> SEQUENCE: 12

Cys Ser Arg Val Ser Ser Gly Cys Glu Phe Lys Asp Ser Val Met Met
 1               5                  10                  15

Gly Ala Asp Ile
            20
```

-continued

<210> SEQ ID NO 13
<211> LENGTH: 20
<212> TYPE: PRT
<213> ORGANISM: Zea mays

<400> SEQUENCE: 13

Cys Ser Arg Val Ser Ser Gly Cys Glu Leu Lys Asp Ser Val Met Met
1               5                   10                  15

Gly Ala Asp Ile
            20

<210> SEQ ID NO 14
<211> LENGTH: 20
<212> TYPE: PRT
<213> ORGANISM: Triticum aestivum

<400> SEQUENCE: 14

Arg Ser Arg Leu Asn Ser Gly Ser Glu Leu Lys Asn Ala Met Met Met
1               5                   10                  15

Gly Ala Asp Ser
            20

<210> SEQ ID NO 15
<211> LENGTH: 20
<212> TYPE: PRT
<213> ORGANISM: Hordeum vulgare

<400> SEQUENCE: 15

Arg Ser Arg Leu Asn Ser Gly Ser Glu Leu Lys Asn Ala Met Met Met
1               5                   10                  15

Gly Ala Asp Ser
            20

<210> SEQ ID NO 16
<211> LENGTH: 12
<212> TYPE: PRT
<213> ORGANISM: Oryza sativa

<400> SEQUENCE: 16

Ser Ser Arg Val Ser Ser Gly Cys Glu Leu Lys Ile
1               5                   10

<210> SEQ ID NO 17
<211> LENGTH: 24
<212> TYPE: PRT
<213> ORGANISM: TS60 Mutant of Zea mays

<400> SEQUENCE: 17

Asp Phe Gly Ser Lys Ile Leu Pro Arg Ala Val Leu Asp His Ser Val
1               5                   10                  15

Gln Ala Cys Ile Phe Thr Gly Tyr
            20

<210> SEQ ID NO 18
<211> LENGTH: 24
<212> TYPE: PRT
<213> ORGANISM: Zea mays

<400> SEQUENCE: 18

Asp Phe Gly Ser Glu Ile Leu Pro Arg Ala Val Leu Asp His Ser Val
1               5                   10                  15

Gln Ala Cys Ile Phe Thr Gly Tyr
            20

<210> SEQ ID NO 19
<211> LENGTH: 24
<212> TYPE: PRT
<213> ORGANISM: Triticum aestivum

<400> SEQUENCE: 19

Asp Phe Gly Ser Glu Ile Leu Pro Arg Ala Leu His Asp His Asn Val
 1               5                  10                  15

Gln Ala Tyr Val Phe Thr Asp Tyr
            20

<210> SEQ ID NO 20
<211> LENGTH: 24
<212> TYPE: PRT
<213> ORGANISM: Hordeum vulgare

<400> SEQUENCE: 20

Asp Phe Gly Ser Glu Ile Leu Pro Arg Ala Leu His Asp His Asn Val
 1               5                  10                  15

Gln Ala Tyr Val Phe Thr Asp Tyr
            20

<210> SEQ ID NO 21
<211> LENGTH: 25
<212> TYPE: PRT
<213> ORGANISM: Oryza sativa

<400> SEQUENCE: 21

Asp Phe Gly Ser Glu Ile Leu Pro Arg Ala Leu Leu Glu His Asn Val
 1               5                  10                  15

Lys Val Ala Cys Val Phe Thr Glu Tyr
            20                  25

<210> SEQ ID NO 22
<211> LENGTH: 25
<212> TYPE: PRT
<213> ORGANISM: TS60 Mutant of Zea mays

<400> SEQUENCE: 22

Glu Asp Val Gly Thr Ile Lys Ser Phe Phe Asp Ala Asn Leu Val Leu
 1               5                  10                  15

Thr Glu Gln Pro Ser Lys Phe Asp Phe
            20                  25

<210> SEQ ID NO 23
<211> LENGTH: 25
<212> TYPE: PRT
<213> ORGANISM: Zea mays

<400> SEQUENCE: 23

Glu Asp Val Gly Thr Ile Lys Ser Phe Phe Asp Ala Asn Leu Ala Leu
 1               5                  10                  15

Thr Glu Gln Pro Ser Lys Phe Asp Phe
            20                  25

<210> SEQ ID NO 24
<211> LENGTH: 25
<212> TYPE: PRT
<213> ORGANISM: Triticum aestivum

```
<400> SEQUENCE: 24

Glu Asp Ile Gly Thr Ile Arg Ser Phe Phe Asp Ala Asn Met Ala Leu
 1               5                  10                  15

Cys Glu Gln Pro Pro Lys Phe Glu Phe
             20                  25

<210> SEQ ID NO 25
<211> LENGTH: 25
<212> TYPE: PRT
<213> ORGANISM: Hordeum vulgare

<400> SEQUENCE: 25

Glu Asp Ile Gly Thr Ile Arg Ser Phe Phe Asp Ala Asn Met Ala Leu
 1               5                  10                  15

Cys Glu Gln Pro Pro Lys Phe Glu Phe
             20                  25

<210> SEQ ID NO 26
<211> LENGTH: 25
<212> TYPE: PRT
<213> ORGANISM: Oryza sativa

<400> SEQUENCE: 26

Glu Asp Ile Gly Thr Ile Lys Ser Phe Phe Asp Ala Asn Leu Ala Leu
 1               5                  10                  15

Thr Glu Gln Pro Pro Lys Phe Glu Phe
             20                  25

<210> SEQ ID NO 27
<211> LENGTH: 20
<212> TYPE: PRT
<213> ORGANISM: RTS48-2 Mutant of Zea mays

<400> SEQUENCE: 27

Thr Gln Met Pro Glu Glu Pro Val Gly Trp Phe Gln Gly Thr Ala Asp
 1               5                  10                  15

Ser Ile Arg Lys
             20

<210> SEQ ID NO 28
<211> LENGTH: 20
<212> TYPE: PRT
<213> ORGANISM: Zea mays

<400> SEQUENCE: 28

Thr Gln Met Pro Glu Glu Pro Ala Gly Trp Phe Gln Gly Thr Ala Asp
 1               5                  10                  15

Ser Ile Arg Lys
             20

<210> SEQ ID NO 29
<211> LENGTH: 20
<212> TYPE: PRT
<213> ORGANISM: Triticum aestivum

<400> SEQUENCE: 29

Thr Gln Met Pro Gly Glu Ala Ala Gly Trp Phe Arg Gly Thr Ala Asp
 1               5                  10                  15

Ala Val Arg Lys
             20
```

```
<210> SEQ ID NO 30
<211> LENGTH: 20
<212> TYPE: PRT
<213> ORGANISM: Hordeum vulgare

<400> SEQUENCE: 30

Thr Gln Met Pro Gly Glu Ala Ala Gly Trp Phe Arg Gly Thr Ala Asp
 1               5                  10                  15

Ala Val Arg Lys
            20

<210> SEQ ID NO 31
<211> LENGTH: 20
<212> TYPE: PRT
<213> ORGANISM: Oryza sativa

<400> SEQUENCE: 31

Thr Gln Met Pro Asp Glu Pro Ala Gly Trp Phe Gln Gly Thr Ala Asp
 1               5                  10                  15

Ala Ile Arg Lys
            20

<210> SEQ ID NO 32
<211> LENGTH: 18
<212> TYPE: PRT
<213> ORGANISM: RTS60-1 Mutant of Zea mays

<400> SEQUENCE: 32

Asp Lys Cys Lys Met Lys Tyr Val Phe Ile Ser Asp Gly Cys Leu Leu
 1               5                  10                  15

Arg Glu

<210> SEQ ID NO 33
<211> LENGTH: 18
<212> TYPE: PRT
<213> ORGANISM: Zea mays

<400> SEQUENCE: 33

Asp Lys Cys Lys Met Lys Tyr Ala Phe Ile Ser Asp Gly Cys Leu Leu
 1               5                  10                  15

Arg Glu

<210> SEQ ID NO 34
<211> LENGTH: 18
<212> TYPE: PRT
<213> ORGANISM: Triticum aestivum

<400> SEQUENCE: 34

Asp Lys Cys Arg Ile Lys Glu Ala Ile Ile Ser His Gly Cys Phe Leu
 1               5                  10                  15

Arg Glu

<210> SEQ ID NO 35
<211> LENGTH: 18
<212> TYPE: PRT
<213> ORGANISM: Hordeum vulgare

<400> SEQUENCE: 35

Asp Lys Cys Arg Ile Lys Glu Ala Ile Ile Ser His Gly Cys Phe Leu
 1               5                  10                  15

Arg Glu
```

```
<210> SEQ ID NO 36
<211> LENGTH: 20
<212> TYPE: PRT
<213> ORGANISM: Oryza sativa

<400> SEQUENCE: 36

Asp Lys Cys Lys Cys Lys Ile Lys Asp Ala Ile Ile Ser Asp Gly Cys
 1               5                  10                  15

Ser Phe Ser Glu
            20
```

NUCLEIC ACIDS ENCODING HEAT STABLE MUTANTS OF PLANT ADP-GLUCOSE PYROPHOSPHORYLASE

CROSS-REFERENCE TO A RELATED APPLICATIONS

This application is a continuation of U.S. application Ser. No. 10/079,478, filed Feb. 19, 2002 now U.S. Pat. No. 6,809,235, which is a continuation-in-part of U.S. application Ser. No. 09/312,433, filed May 14, 1999, now U.S. Pat. No. 6,403,863, which is a continuation-in-part of U.S. application Ser. No. 08/972,545, filed Nov. 18, 1997, now U.S. Pat. No. 6,069,300, and U.S. application Ser. No. 09/312,433 claims the benefit of U.S. Provisional Application No. 60/085,460, filed May 14, 1998, and U.S. application Ser. No. 08/972,545 claims the benefit of U.S. Provisional Application No. 60/031,045, filed Nov. 18, 1996.

This invention was made with government support under National Science Foundation grant number 9316887. The government has certain rights in the invention.

BACKGROUND OF THE INVENTION

The sessile nature of plant life generates a constant exposure to environmental factors that exert positive and negative effects on plant growth and development. One of the major impediments facing modem agriculture is adverse environmental conditions. One important factor which causes significant crop loss is heat stress. Temperature stress greatly reduces grain yield in many cereal crops such as maize, wheat, and barley. Yield decreases due to heat stress range from 7 to 35% in the cereals of world-wide importance.

A number of studies have identified likely physiological consequences of heat stress. Early work by Hunter et al. (Hunter, R. B., Tollenaar, M., and Breuer, C. M. [1977] *Can. J. Plant Sci*. 57:1127-1133) using growth chamber conditions showed that temperature decreased the duration of grain filling in maize. Similar results in which the duration of grain filling was adversely altered by increased temperatures were identified by Tollenaar and Bruulsema (Tollenaar, M. and Bruulsema, T. W. [1988] *Can. J. Plant Sci*. 68:935-940). Badu-Apraku et al. (Badu-Apraku, B., Hunter, R. B., and Tollenaar, M. [1983] *Can. J. Plant. Sci*. 63:357-363) measured a marked reduction in the yield of maize plants grown under the day/night temperature regime of 35/15° C. compared to growth in a 25/15° C. temperature regime. Reduced yields due to increased temperatures is also supported by historical as well as climatological studies (Thompson, L. M. [1986] *Agron. J*. 78:649-653; Thompson, L. M. [1975] *Science* 188:535-541; Chang, J. [1981] *Agricul. Metero*. 24:253-262; and Conroy, J. P., Seneweera, S., Basra, A. S., Rogers, G., and Nissen-Wooller, B. [1994] *Aust. J. Plant Physiol*. 21:741-758).

That the physiological processes of the developing seed are adversely affected by heat stress is evident from studies using an in vitro kernel culture system (Jones, R. J., Gengenbach, B. G., and Cardwell, V. B. [1981] *Crop Science* 21:761-766; Jones, R. J., Ouattar, S., and Crookston, R. K. [1984] *Crop Science* 24:133-137; and Cheikh, N., and Jones, R. J. [1995] *Physiol. Plant*. 95:59-66). Maize kernels cultured at the above-optimum temperature of 35° C. exhibited a dramatic reduction in weight.

Work with wheat identified the loss of soluble starch synthase (SSS) activity as a hallmark of the wheat endosperm's response to heat stress (Hawker, J. S. and Jenner, C. F. [1993] *Aust. J. Plant Physiol*. 20:197-209; Denyer, K., Hylton, C. M., and Smith, A. M. [1994] *Aust. J. Plant Physiol*. 21:783-789; Jenner, C. F. [1994] *Aust. J. Plant Physiol*. 21:791-806). Additional studies with SSS of wheat endosperm show that it is heat labile (Rijven, A. H. G. C. [1986] *Plant Physiol*. 81:448-453; Keeling, P. L., Bacon, P. J., Holt, D. C. [1993] *Planta*. 191:342-348; Jenner, C. F., Denyer, K., and Guerin, J. [1995] *Aust. J. Plant Physiol*. 22:703-709).

The roles of SSS and ADP glucose pyrophosphorylase (AGP) under heat stress conditions in maize is less clear. (AGP) catalyzes the conversion of ATP and α-glucose-1-phosphate to ADP-glucose and pyrophosphate. ADP-glucose is used as a glycosyl donor in starch biosynthesis by plants and in glycogen biosynthesis by bacteria. The importance of ADP-glucose pyrophosphorylase as a key enzyme in the regulation of starch biosynthesis was noted in the study of starch deficient mutants of maize (*Zea mays*) endosperm (Tsai, C. Y., and Nelson, Jr., O. E. [1966] *Science* 151:341-343; Dickinson, D. B., J. Preiss [1969] *Plant Physiol*. 44:1058-1062).

Ou-Lee and Setter (Ou-Lee, T. and Setter, T. L. [1985] *Plant Physiol*. 79:852-855) examined the effects of temperature on the apical or tip regions of maize ears. With elevated temperatures, AGP activity was lower in apical kernels when compared to basal kernels during the time of intense starch deposition. In contrast, in kernels developed at normal temperatures, AGP activity was similar in apical and basal kernels during this period. However, starch synthase activity during this period was not differentially affected in apical and basal kernels. Further, heat-treated apical kernels exhibited an increase in starch synthase activity over control. This was not observed with AGP activity. Singletary et al. (Singletary, G. W., Banisadr, R., and Keeling, P. L. [1993] *Plant Physiol*. 102:6 (suppl); Singletary, G. W., Banisadra, R., Keeling, P. L. [1994] *Aust. J. Plant Physiol*. 21:829-841) using an in vitro culture system quantified the effect of various temperatures during the grain fill period. Seed weight decreased steadily as temperature increased from 22-36° C. A role for AGP in yield loss is also supported by work from Duke and Doehlert (Duke, E. R. and Doehlert, D. C. [1996] *Environ. Exp. Botany*. 36:199-208).

Work by Keeling et al. (1994, supra) quantified SSS activity in maize and wheat using $Q_{10}$ analysis, and showed that SSS is an important control point in the flux of carbon into starch.

In vitro biochemical studies with AGP and SSS clearly show that both enzymes are heat labile. Maize endosperm AGP loses 96% of its activity when heated at 57° C. for five minutes (Hannah, L. C., Tuschall, D. M., and Mans, R. J. [1980] *Genetics* 95:961-970). This is in contrast to potato AGP which is fully stable at 70° C. (Sowokinos, J. R. and Preiss, J. [1982] *Plant Physiol*. 69:1459-1466; Okita, T. W., Nakata, P. A., Anderson, J. M., Sowokinos, J., Morell, J., and Preiss, J. [1990] *Plant Physiol*. 93:785-90). Heat inactivation studies with SSS showed that it is also labile at higher temperatures, and kinetic studies determined that the Km value for amylopectin rose exponentially when temperature increased from 25-45° C. (Jenner et al., 1995, supra).

Biochemical and genetic evidence has identified AGP as a key enzyme in starch biosynthesis in higher plants and glycogen biosynthesis in *E. coli* (Preiss, J. and Romeo, T. [1994] *Progress in Nuc. Acid Res. and Mol Biol*. 47:299-329; Preiss, J. and Sivak, M. [1996] "Starch synthesis in sinks and sources," In *Photoassimilate distribution in plants and crops: source-sink relationships*. Zamski, E., ed., Marcil Dekker Inc. pp. 139-168). AGP catalyzes what is viewed as the initial step in the starch biosynthetic pathway with the product of the reaction being the activated glucosyl donor, ADPglucose. This is utilized by starch synthase for extension of the polysaccharide polymer (reviewed in Hannah, L. Curtis [1996] "Starch synthesis in the maize endosperm," In: *Advances in Cellular and Molecular Biology of Plants*, Vol. 4. B. A. Larkins and I. K. Vasil (eds.). Cellular and Molecular Biology of Plant Seed Development. Kluwer Academic Publishers, Dordrecht, The Netherlands).

Initial studies with potato AGP showed that expression in *E. coli* yielded an enzyme with allosteric and kinetic properties very similar to the native tuber enzyme (Iglesias, A., Barry, G. F., Meyer, C., Bloksberg, L., Nakata, P., Greene, T., Laughlin, M. J., Okita, T. W., Kishore, G. M., and Preiss, J. [1993] *J. Biol Chem*. 268:1081-86; Ballicora, M. A., Laughlin, M. J., Fu, Y., Okita, T. W., Barry, G. F., and Preiss, J. [1995] *Plant Physiol*. 109:245-251). Greene et al. (Greene, T. W., Chantler, S. E., Kahn, M. L., Barry, G. F., Preiss, J., and Okita, T. W. [1996] *Proc. Natl. Acad. Sci*. 93:1509-1513; Greene, T. W., Woodbury, R. L., and Okita, T. W. [1996] *Plant Physiol*. (112:1315-1320) showed the usefulness of the bacterial expression system in their structure-function studies with the potato AGP. Multiple mutations important in mapping allosteric and substrate binding sites were identified (Okita, T. W., Greene, T. W., Laughlin, M. J., Salamone, P., Woodbury, R., Choi, S., Ito, H., Kavakli, H., and Stephens, K. [1996] "Engineering Plant Starches by the Generation of Modified Plant Biosynthetic Enzymes," *In Engineering Crops for Industrial End Uses*, Shewry, P. R., Napier, J. A., and Davis, P., eds., Portland Press Ltd., London).

AGP enzymes have been isolated from both bacteria and plants. Bacterial AGP consists of a homotetramer, while plant AGP from photosynthetic and non-photosynthetic tissues is a heterotetramer composed of two different subunits. The plant enzyme is encoded by two different genes, with one subunit being larger than the other. This feature has been noted in a number of plants. The AGP subunits in spinach leaf have molecular weights of 54 kDa and 51 kDa, as estimated by SDS-PAGE. Both subunits are immunoreactive with antibody raised against purified AGP from spinach leaves (Copeland, L., J. Preiss (1981) *Plant Physiol*. 68:996-1001; Morell, M., M. Bloon, V. Knowles, J. Preiss [1988] *J. Bio. Chem*. 263:633). Immunological analysis using antiserum prepared against the small and large subunits of spinach leaf showed that potato tuber AGP is also encoded by two genes (Okita et al., 1990, supra). The cDNA clones of the two subunits of potato tuber (50 and 51 kDa) have also been isolated and sequenced (Muller-Rober, B. T., J. Kossmann, L. C. Hannah, L. Willmitzer, U. Sounewald [1990] *Mol. Gen. Genet*. 224:136-146; Nakata, P. A., T. W. Greene, J. M. Anderson, B. J. Smith-White, T. W. Okita, J. Preiss [1991] *Plant Mol. Biol*. 17:1089-1093). The large subunit of potato tuber AGP is heat stable (Nakata et al. [1991], supra).

As Hannah and Nelson (Hannah, L. C., O. E. Nelson (1975) *Plant Physiol*. 55:297-302; Hannah, L. C., and Nelson, Jr., O. E. [1976] *Biochem. Genet*. 14:547-560) postulated, both Shrunken-2 (Sh2) (Bhave, M. R., S. Lawrence, C. Barton, L. C. Hannah [1990] *Plant Cell* 2:581-588) and Brittle-2 (Bt2) (Bae, J. M., M. Giroux, L. C. Hannah [1990] *Maydica* 35:317-322) are structural genes of maize endosperm ADP-glucose pyrophosphorylase. Sh2 and Bt2 encode the large subunit and small subunit of the enzyme, respectively. From cDNA sequencing, Sh2 and Bt2 proteins have predicted molecular weight of 57,179 Da (Shaw, J. R., L. C. Hannah [1992] *Plant Physiol*. 98:1214-1216) and 52,224 Da, respectively. The endosperm is the site of most starch deposition during kernel development in maize. Sh2 and Bt2 maize endosperm mutants have greatly reduced starch levels corresponding to deficient levels of AGP activity. Mutations of either gene have been shown to reduce AGP activity by about 95% (Tsai and Nelson, 1966, supra; Dickinson and Preiss, 1969, supra). Furthermore, it has been observed that enzymatic activities increase with the dosage of functional wild type Sh2 and Bt2 alleles, whereas mutant enzymes have altered kinetic properties. AGP is the rate limiting step in starch biosynthesis in plants. Stark et al. placed a mutant form of *E. coli* AGP in potato tuber and obtained a 35% increase in starch content (Stark et al. [1992] *Science* 258:287).

The cloning and characterization of the genes encoding the AGP enzyme subunits have been reported for various plants. These include Sh2 cDNA (Bhave et al., 1990, supra), Sh2 genomic DNA (Shaw and Hannah, 1992, supra), and Bt2 cDNA (Bae et al., 1990, supra) from maize; small subunit cDNA (Anderson, J. M., J. Hnilo, R. Larson, T. W. Okita, M. Morell, J. Preiss [1989] *J. Biol. Chem*. 264:12238-12242) and genomic DNA (Anderson, J. M., R. Larson, D. Landencia, W. T. Kim, D. Morrow, T. W. Okita, J. Preiss [1991] *Gene* 97:199-205) from rice; and small and large subunit cDNAs from spinach leaf (Morell et al., 1988, supra) and potato tuber (Muller-Rober et al., 1990, supra; Nakata, P A., Greene, T. W., Anderson, J. W., Smith-White, B. J., Okita, T. W., and Preiss, J. [1991] *Plant Mol. Biol*. 17:1089-1093). In addition, cDNA clones have been isolated from wheat endosperm and leaf tissue (Olive, M. R., R. J. Ellis, W. W. Schuch [1989] *Plant Physiol. Mol. Biol*. 12:525-538) and *Arabidopsis thaliana* leaf (Lin, T., Caspar, T., Sommerville, C. R., and Preiss, J. [1988] *Plant Physiol*. 88:1175-1181).

AGP functions as an allosteric enzyme in all tissues and organisms investigated to date. The allosteric properties of AGP were first shown to be important in *E. coli*. A glycogen-overproducing *E. coli* mutant was isolated and the mutation mapped to the structural gene for AGP, designated as glyC. The mutant *E. coli*, known as glyC-16, was shown to be more sensitive to the activator, fructose 1,6 bisphosphate, and less sensitive to the inhibitor, cAMP (Preiss, J. [1984] *Ann. Rev. Microbiol*. 419-458). Although plant AGP's are also allosteric, they respond to different effector molecules than bacterial AGP's. In plants, 3-phosphoglyceric acid (3-PGA) functions as an activator while phosphate ($PO_4$) serves as an inhibitor (Dickinson and Preiss, 1969, supra).

Using an in vivo mutagenesis system created by the Ac-mediated excision of a Ds transposable element fortuitously located close to a known activator binding site, Giroux et al. (Giroux, M. J., Shaw, J., Barry, G., Cobb, G. B., Greene, T., Okita, T. W., and Hannah, L. C. [1996] *Proc. Natl. Acad. Sci*. 93:5824-5829) were able to generate site-specific mutants in a functionally important region of maize endosperm AGP. One mutant, Rev 6, contained a tyrosine-serine insert in the large subunit of AGP and conditioned a 11-18% increase in seed weight. In addition, published international application WO 01/64928 teaches that various characteristics, such as seed number, plant biomass, Harvest Index etc., can be increased in plants transformed with a polynucleotide encoding a large subunit of maize AGP containing the Rev6 mutation.

BRIEF SUMMARY OF THE INVENTION

The subject invention pertains to materials and methods useful for improving crop yields in plants, such as those plants that produce cereal crops. In one embodiment, the subject invention provides heat stable AGP enzymes and nucleotide sequences which encode these enzymes. In a preferred embodiment, the heat stable enzymes of the invention can be used to provide plants having greater tolerance to higher temperatures, thus enhancing the crop yields from these plants. In a particularly preferred embodiment, the improved plant is a cereal. Cereals to which this invention applies include, for example, maize, wheat, rice, and barley.

BRIEF DESCRIPTION OF THE DRAWINGS

FIG. 2 shows primary sequence alignment of the region surrounding HS 33 mutation (SEQ ID NO: 1) in the AGP large subunits for maize (SEQ ID NO: 2), wheat (SEQ ID NO: 3), barley (SEQ ID NO: 4), and potato (SEQ ID NO: 5). Conserved regions are boxed.

FIG. 3 shows primary sequence alignment of the region surrounding HS 40 mutation (SEQ ID NO: 6) in the AGP large subunits for maize (SEQ ID NO: 7), wheat (SEQ ID NO: 8), barley (SEQ ID NO: 9), and potato (SEQ ID NO: 10). Conserved regions are boxed. Bolded aspartic acid residue corresponds to D413A allosteric mutant of potato LS (Greene, T. W., Woodbury, R. L., and Okita, T. W. [1996] *Plant Physiol*. (112:1315-1320). Spinach leaf AGP sequence (SEQ ID NO: 11) is the activator site 2 peptide identified in 3-PGA analogue studies (Ball, K. and Preiss, J. [1994] *J. Biol. Chem*. 269:24706-24711). The labeled lysine residue is bolded.

FIGS. 4A and 4B show molecular characterization of TS48 (SEQ ID NO: 12) and TS60 (SEQ ID NO: 17), respectively. Genetic lesion of TS48 (SEQ ID NO: 12) and corresponding residues are in bold. The amino acid number is indicated above the Leu to Phe mutation of TS48 (SEQ ID NO: 12). The last line is a consensus sequence. The Leu residue is highly conserved. Genetic lesions of TS60 (SEQ ID NO: 17) and corresponding residues are in bold. The amino acid numbers are indicated above the Glu to Lys and Ala to Val mutations of TS60 (SEQ ID NO: 17). Boxed residues correspond to the HS 33 mutation (SEQ ID NO: 1) previously identified and shown to be important in heat stability of the maize endosperm AGP. The last line is a consensus sequence.

FIGS. 5A and 5B show molecular characterization of RTS 48-2 (SEQ ID NO: 27) and RTS 60-1 (SEQ ID NO: 32), respectively. Genetic lesion of RTS 48-2 (SEQ ID NO: 27) and corresponding residues are in bold. The amino acid number is indicated above the Ala to Val mutation of RTS 48-2 (SEQ ID NO: 27). The last line is a consensus sequence. Of significance, the mutation identified in RTS 48-2 (SEQ ID NO: 27) maps to the identical residue found in the heat stable variant HS13. HS 13 contained an Ala to Pro mutation at position 177. Genetic lesion of RTS 60-1 (SEQ ID NO: 32) and corresponding residues are in bold. The amino acid number is indicated above the Ala to Val mutation of RTS 60-1 (SEQ ID NO: 32). The last line is a consensus sequence.

BRIEF DESCRIPTION OF THE SEQUENCES

Figure 1:
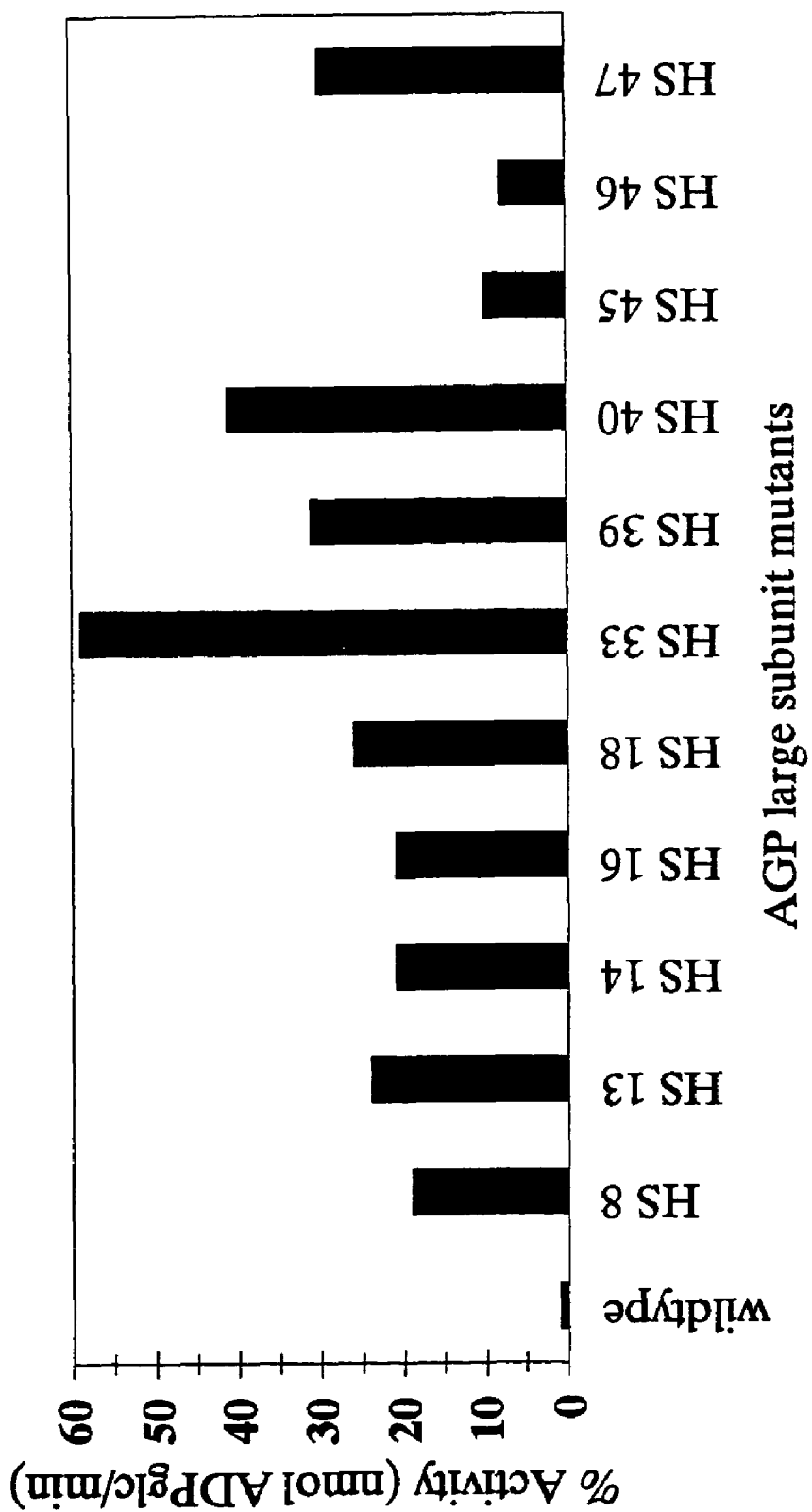
FIG. 1 shows heat stable maize endosperm AGP large subunit mutants. Percentage of AGP activity remaining after five minutes of heat treatment at 60° C. is shown.

SEQ ID NO. 1 is an amino acid sequence of a region of the large subunit of AGP in maize containing the HS 33 mutation as shown in FIG. 2.

SEQ ID NO. 2 is an amino acid sequence of a region of the large subunit of AGP in maize as shown in FIG. 2.

SEQ ID NO. 3 is an amino acid sequence of a region of the large subunit of AGP in wheat as shown in FIG. 2.

SEQ ID NO. 4 is an amino acid sequence of a region of the large subunit of AGP in barley as shown in FIG. 2.

SEQ ID NO. 5 is an amino acid sequence of a region of the large subunit of AGP in potato as shown in FIG. 2.

SEQ ID NO. 6 is an amino acid sequence of a region of the large subunit of AGP in maize containing the HS40 mutation as shown in FIG. 3.

SEQ ID NO. 7 is an amino acid sequence of a region of the large subunit of AGP in maize as shown in FIG. 3.

SEQ ID NO. 8 is an amino acid sequence of a region of the large subunit of AGP in wheat as shown in FIG. 3.

SEQ ID NO. 9 is an amino acid sequence of a region of the large subunit of AGP in barley as shown in FIG. 3.

SEQ ID NO. 10 is an amino acid sequence of a region of the large subunit of AGP in potato as shown in FIG. 3.

SEQ ID NO. 11 is an amino acid sequence of a region of the large subunit of AGP in spinach as shown in FIG. 3.

SEQ ID NO. 12 is an amino acid sequence of a region of the large subunit of AGP in maize containing the TS48 mutation as shown in FIG. 4A.

SEQ ID NO. 13 is an amino acid sequence of a region of the large subunit of AGP in maize as shown in FIG. 4A.

SEQ ID NO. 14 is an amino acid sequence of a region of the large subunit of AGP in wheat as shown in FIG. 4A.

SEQ ID NO. 15 is an amino acid sequence of a region of the large subunit of AGP in barley as shown in FIG. 4A.

SEQ ID NO. 16 is an amino acid sequence of a region of the large subunit of AGP in rice as shown in FIG. 4A.

SEQ ID NO. 17 is an amino acid sequence of a region of the large subunit of AGP in maize containing the TS60 mutation as shown in FIG. 4B.

SEQ ID NO. 18 is an amino acid sequence of a region of the large subunit of AGP in maize as shown in FIG. 4B.

SEQ ID NO. 19 is an amino acid sequence of a region of the large subunit of AGP in wheat as shown in FIG. 4B.

SEQ ID NO. 20 is an amino acid sequence of a region of the large subunit of AGP in barley as shown in FIG. 4B.

SEQ ID NO. 21 is an amino acid sequence of a region of the large subunit of AGP in rice as shown in FIG. 4B.

SEQ ID NO. 22 is an amino acid sequence of a region of the large subunit of AGP in maize containing the TS60 mutation as shown in FIG. 4B.

SEQ ID NO. 23 is an amino acid sequence of a region of the large subunit of AGP in maize as shown in FIG. 4B.

SEQ ID NO. 24 is an amino acid sequence of a region of the large subunit of AGP in wheat as shown in FIG. 4B.

SEQ ID NO. 25 is an amino acid sequence of a region of the large subunit of AGP in barley as shown in FIG. 4B.

SEQ ID NO. 26 is an amino acid sequence of a region of the large subunit of AGP in rice as shown in FIG. 4B.

SEQ ID NO. 27 is an amino acid sequence of a region of the large subunit of AGP in maize containing the RTS48-2 mutation as shown in FIG. 5A.

SEQ ID NO. 28 is an amino acid sequence of a region of the large subunit of AGP in maize as shown in FIG. 5A.

SEQ ID NO. 29 is an amino acid sequence of a region of the large subunit of AGP in wheat as shown in FIG. 5A.

SEQ ID NO. 30 is an amino acid sequence of a region of the large subunit of AGP in barley as shown in FIG. 5A.

SEQ ID NO. 31 is an amino acid sequence of a region of the large subunit of AGP in rice as shown in FIG. 5A.

SEQ ID NO. 32 is an amino acid sequence of a region of the large subunit of AGP in maize containing the RTS60-1 mutation as shown in FIG. 5B.

SEQ ID NO. 33 is an amino acid sequence of a region of the large subunit of AGP in maize as shown in FIG. 5B.

SEQ ID NO. 34 is an amino acid sequence of a region of the large subunit of AGP in wheat as shown in FIG. 5B.

SEQ ID NO. 35 is an amino acid sequence of a region of the large subunit of AGP in barley as shown in FIG. 5B.

SEQ ID NO. 36 is an amino acid sequence of a region of the large subunit of AGP in rice as shown in FIG. 5B.

SEQ ID NO. 37 is an amino acid sequence of a mutant maize large subunit of AGP.

SEQ ID NO. 38 is an amino acid sequence of a mutant maize large subunit of AGP.

SEQ ID NO. 39 is an amino acid sequence of a mutant maize large subunit of AGP.

DETAILED DISCLOSURE OF THE INVENTION

The subject invention concerns novel mutant polynucleotide molecules, and the polypeptides encoded thereby, that confer increased yield in plants grown under conditions of heat stress relative to plants having wild type genotype. In specific embodiments, the polynucleotide molecules of the subject invention encode maize endosperm ADP glucose pyrophosphorylase (AGP) and soluble starch synthase (SSS) enzyme activities. The mutant enzymes confer increased stability to heat stress conditions during seed and plant development in seeds and plant tissue expressing the enzymes as compared with wild type enzyme activities.

In one embodiment, a polynucleotide of the present invention encodes a mutant large subunit of maize AGP containing a histidine-to-tyrosine amino acid substitution in the sequence of the polypeptide. This substitution occurs at amino acid residue number 333, according to the accepted number of the amino acids in this protein (Shaw and Hannah, 1992, supra). The position of this substitution can be readily identified by a person skilled in the art. A second mutation exemplified in the subject invention is a threonine-to-isoleucine substitution at position number 460 of the large subunit of the maize AGP protein.

Also exemplified are mutants wherein the histidine at position 333 of the maize large subunit of AGP is replaced with a phenylalanine, methionine, or glycine. Additional exemplified maize AGP large subunit mutants conferring increased heat stability are shown below in Table 1.

TABLE 1

| Mutant | Amino Acid Change |
| --- | --- |
| HS 13 | Ala to Pro at position 177 |
| HS 14 | Asp to His at position 400, and Val to Ile at position 454 |
| HS 16 | Arg to Thr at position 104 |
| HS 33 | His to Tyr at position 333 |
| HS 33F | His to Phe at position 333 |
| HS 33M | His to Met at position 333 |
| HS 33G | His to Gly at position 333 |
| HS 39 | His to Tyr at position 333 |
| HS 40 | His to Tyr at position 333, and Thr to Ile at position 460 |
| HS 47 | Arg to Pro at position 216, and His to Tyr at position 333 |
| RTS 48-2 | Ala to Val at position 177 |
| RTS 60-1 | Ala to Val at position 396 |

Because of the homology of AGP polypeptides between various species of plants (Smith-White and Preiss [1992] *J. Mol. Evol.* 34:449-464), the ordinarily skilled artisan can readily determine the corresponding position of the mutations for maize AGP exemplified herein in AGP from plants other than maize. For example, FIGS. 2 and 3 show primary sequence alignment for the region around the maize HS 33 and HS 40 mutations in wheat, barley, and potato. Thus, the present invention encompasses polynucleotides that encode mutant AGP of plants other than maize, including, but not limited to, wheat, barley, and rice, that confers increased heat stability when expressed in the plant.

cDNA clones for the subunits of the maize endosperm AGP (SH2 and BT2) and an *E. coli* strain deficient in the endogenous bacterial AGP (glg C⁻) (AC70R1-504) have facilitated the establishment of a bacterial expression system to study the maize endosperm AGP. Expression of a single subunit is unable to complement the glg C⁻ mutant, and no glycogen is produced (Iglesias, A., Barry, G. F., Meyer, C., Bloksberg, L., Nakata, P., Greene, T., Laughlin, M. J., Okita, T. W., Kishore, G. M., and Preiss, J. [1993] *J. Biol Chem.* 268: 1081-86). However, expression of both the large and small subunits on compatible expression vectors fully complements the glg C⁻ mutation and restores glycogen production as evidenced by a dark, reddish-brown staining of colonies exposed to iodine. Thus, complementation is easily identified by simply exposing the colonies to iodine.

In one embodiment, *E. coli* glg C⁻ cells expressing the structural genes for either potato or maize endosperm AGP were used. Cells containing potato AGP genes can synthesize copious levels of glycogen when grown at 37° C. or at 42° C. However, cells expressing maize endosperm AGP only synthesize glycogen at 37° C. This result demonstrates the heat sensitivity of wild-type maize endosperm AGP. That there is a difference between potato and maize AGP's in this regard provides an efficient system for screening for mutant cells that have heat stable variants of the maize endosperm AGP.

One aspect of the subject invention pertains to the efficient identification of AGP which is heat stable. Accordingly, a plasmid comprising a polynucleotide coding for the SH2 subunit of maize AGP was chemically mutagenized, as described below, placed into mutant *E. coli* cells expressing the BT2 subunit, and the cells grown at 42° C. to select for mutants that could produce glycogen at that temperature. Other mutagens known in the art can also be used. Eleven heritable, iodine staining mutants, termed heat stable (HS) mutants, were isolated. Crude extracts of these mutants were prepared and the heat stability of the resulting AGP was monitored. The mutants retained between 8-59% of their activity after incubation at 60° C. for five minutes (FIG. 1). This compares to the 1-4% routinely observed for wild-type AGP at this temperature.

The results show that heat stable forms of enzymes can be created according to the subject invention by mutation. Thus, one aspect of the invention pertains to processes for producing and identifying polynucleotides encoding mutant starch biosynthesis enzymes having increased heat stability compared to wild type enzymes. Unexpectedly, total activity of the maize endosperm AGP before heat treatment was elevated about two- to three-fold in the majority of these mutants. This surprising result makes these mutants particularly advantageous for use in agriculture. Mutagenesis techniques as described herein can be used according to the subject invention to identify other genes encoding heat stable starch biosynthesis enzymes.

The genes encoding several of the heat stable mutants exemplified herein, including two of the most heat stable HS mutants, HS 33 and HS 40, were completely sequenced. HS 33, which retains 59% of its activity after heat treatment, contains a single base pair mutation that changes a histidine residue at position 333 of the amino acid sequence of the polypeptide to a tyrosine (FIG. 2). Primary sequence alignments with the large subunits from wheat and barley AGPs show that a histidine is also present at the analogous residue (FIG. 3) (Ainsworth, C., Hosein, F., Tarvis, M., Weir, F., Burrell, M., Devos, K. M., Gale, M. D. [1995] *Planta* 197:1-10). Sequence analysis of HS 40, which retains 41% of its activity post heat treatment, also contained a histidine to tyrosine mutation at position 333. An additional point mutation was identified that generated a threonine to isoleucine substitution. The threonine residue is highly conserved in AGP large subunits, while in AGP small subunits the analogous residue is either a cysteine or serine (Ainsworth et al., 1995, supra). The threonine to isoleucine substitution is located close to the carboxyl terminus of the large subunit, and close to a known binding site for the activator 3-PGA (FIG. 3).

Another aspect of the present invention pertains to mutant starch biosynthesis enzymes, such as AGP, and the polynucleotides that encode them, wherein these mutant enzymes are isolated by selecting for temperature sensitive (TS) mutants which are then mutagenized and screened for revertants that show enhanced stability. A further aspect of the invention concerns the methods for producing and identifying the polynucleotides and mutant enzymes encoded thereby.

The subject invention also concerns heat stable mutants of AGP that have mutations in the small subunit of the enzyme. Also encompassed within the scope of the invention are polynucleotides that encode the mutant small subunits of AGP. Mutations in the small subunit of AGP that confer heat stability to the enzyme can also be readily prepared and identified using the methods of the subject invention.

Plants and plant tissue bred to contain or transformed with the mutant polynucleotides of the invention, and expressing the polypeptides encoded by the polynucleotides, are also contemplated by the present invention. Plants and plant tissue expressing the mutant polynucleotides produce tissues that have, for example, lower heat-induced loss in weight or yield when subjected to heat stress during development. Plants within the scope of the present invention include monocotyledonous plants, such as rice, wheat, barley, oats, sorghum, maize, lilies, and millet, and dicotyledonous plants, such as peas, alfalfa, chickpea, chicory, clover, kale, lentil, prairie grass, soybean, tobacco, potato, sweet potato, radish, cabbage, rape, apple trees, and lettuce. In a particularly preferred embodiment, the plant is a cereal. Cereals to which this invention applies include, for example, maize, wheat, rice, barley, oats, rye, and millet.

Plants having mutant polynucleotides of the invention can be grown from seeds that comprise a mutant gene in their genome. In addition, techniques for transforming plants with a gene are known in the art.

Because of the degeneracy of the genetic code, a variety of different polynucleotide sequences can encode each of the variant AGP polypeptides disclosed herein. In addition, it is well within the skill of a person trained in the art to create alternative polynucleotide sequences encoding the same, or essentially the same, polypeptides of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the AGP mutant polynucleotide described herein.

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. Allelic variations of the exemplified sequences also come within the scope of the subject invention. The polynucleotide sequences falling within the scope of the subject invention further include sequences which specifically hybridize with the exemplified sequences. The polynucleotide includes both the sense and antisense strands as either individual strands or in the duplex.

Substitution of amino acids other than those specifically exemplified in the mutants disclosed herein are also contemplated within the scope of the present invention. Amino acids can be placed in the following classes: non-polar, uncharged polar, basic, and acidic. Conservative substitutions whereby a mutant AGP polypeptide having an amino acid of one class is replaced with another amino acid of the same class fall within the scope of the subject invention so long as the mutant AGP polypeptide having the substitution still retains increased heat stability relative to a wild type polypeptide. Table 2 below provides a listing of examples of amino acids belonging to each class.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

For example, substitution of the tyrosine at position 333 in the HS 33, HS 39, HS 40 and HS 47 mutant maize endosperm AGP with other amino acids, such as Glycine, Serine, Threonine, Cysteine, Asparagine, and Glutamine, are encompassed within the scope of the invention. Amino acid substitutions at positions other than the site of the heat stable mutation are also contemplated within the scope of the invention so long as the polypeptide retains increased heat stability relative to wild type polypeptides.

The subject invention also concerns polynucleotides which encode fragments of the full length mutant polypeptide, so long as those fragments retain substantially the same functional activity as full length polypeptide. The fragments of mutant AGP polypeptide encoded by these polynucleotides are also within the scope of the present invention.

The subject invention also contemplates those polynucleotide molecules encoding starch biosynthesis enzymes having sequences which are sufficiently homologous with the wild type sequence so as to permit hybridization with that sequence under standard high-stringency conditions. Such hybridization conditions are conventional in the art (see, e.g., Maniatis, T., E. F. Fritsch, J. Sambrook [1989] *Molecular Cloning: A Laboratory Manual*, 2nd Edition, Cold Spring Harbor Laboratory, Cold Spring Harbor, N.Y.).

The polynucleotide molecules of the subject invention can be used to transform plants to express the mutant heat stable enzyme in those plants. In addition, the polynucleotides of the subject invention can be used to express the recombinant variant enzyme. They can also be used as a probe to detect related enzymes. The polynucleotides can also be used as DNA sizing standards.

The polynucleotide molecules of the subject invention also include those polynucleotides that encode starch biosynthesis enzymes, such as AGP enzymes, that contain mutations that can confer increased seed weight, in addition to enhanced heat stability, to a plant expressing these mutants. The combination of a heat stabilizing mutation, such as for example HS 33 or HS 40, with a mutation conferring increased seed weight, e.g., Rev 6, in a polynucleotide that encodes the large subunit of maize AGP is specifically contemplated in the present invention. U.S. Pat. Nos. 5,589,618 and 5,650,557 disclose polynucleotides (e.g., Rev6) that encode mutations in the large subunit of AGP that confer increased seed weight in plants that express the mutant polypeptide.

Mutations in the AGP subunits that confer heat stability can be combined according to the subject invention with phosphate insensitive mutants of maize, such as the Rev6 mutation, to enhance the stability of the Rev6 encoded large subunit.

It is expected that enzymic activity of SSS will be impaired at higher temperatures as observed with AGP. Thus, mutagenized forms of SSS can be expressed under increased thermal conditions (42° C.), to isolate heat stable variants in accordance with the methods described herein. These heat stable mutagenized forms of SSS, and the polynucleotides that encode them, are further aspects of the subject invention.

The subject invention also concerns methods for increasing yield characteristics of plants under conditions of heat stress by incorporating a polynucleotide of the present invention that comprises a mutation in a starch biosynthesis enzyme that confers increased stability or resistance to heat stress conditions and a mutation that confers increased yield characteristics on the plant. Increased yield characteristics include, for example, increased seed number, increased seed weight, increased plant biomass, and increased Harvest Index.

The subject invention also concerns methods for producing and identifying polynucleotides and polypeptides contemplated within the scope of the invention. In one embodiment, gene mutation, followed by selection using a bacterial expression system, can be used to isolate polynucleotide molecules that encode enzymes that can alleviate heat-induced loss in starch synthesis in plants. In a specific embodiment, a method for identifying a polynucleotide encoding a mutant starch biosynthesis protein wherein the mutant starch biosynthesis protein exhibits increased heat stability relative to a wild type protein comprises mutating a polynucleotide encoding a starch biosynthesis protein, expressing the mutated polynucleotide in a cell to produce a mutant starch biosynthesis protein, and determining whether the mutant starch biosynthesis protein exhibits increased heat stability relative to the wild type starch biosynthesis protein.

All patents, patent applications, provisional applications, and publications referred to or cited herein are hereby incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Use of Mutagenesis to Obtain Maize Endosperm AGP Heat Stable Variants

The chemical mutagen hydroxylamine-HCl was initially used for the random mutagenesis of the large subunit expression plasmid. Hydroxylamine preferentially hydroxylates the amino nitrogen at the C-4 position of cytosine, and leads to a GC to AT transition (Suzuki, D. T., Griffith, A. J. F., Miller, J. H., and Lewontin, R. C. [1989] In *Introduction to genetic analysis*, Freeman, NY, 4th ed., pp. 475-499). The chemical mutagen was chosen for its high mutation frequency. Limitations of the chemical mutagen are recognized, and if a large variety of genetic variants are not isolated, PCR based random mutagenesis can be performed. PCR mutagenesis generates a broader spectrum of mutations that include similar frequencies of transitions and transversion, and provides an excellent alternative to the chemical method. The method outlined by Cadwell and Joyce (Cadwell, R. C. and Joyce, G. F. [1992] *PCR Methods and Applications* 2:28-33) can be followed for the PCR based method.

Since the complete expression plasmid is used in the random mutagenesis, it is possible that mutations will occur outside of the coding region. Although it is expected that such mutations will not have any effect on the heat stability of the maize endosperm AGP, each variant can be subcloned into an unmutated expression plasmid before any additional characterization at the enzyme level is conducted. Both the large and small subunit expression plasmids can be constructed so that a NcoI/SacI digestion will liberate the complete coding region. This can easily be cloned back into a unmutated NcoI/SacI digested expression plasmid.

EXAMPLE 2

Molecular Characterization and Analysis of Heat Stable AGP Variants

Initially, 11 heat stable variants of the maize endosperm large subunit were obtained. Sequencing was performed using DuPont and ABI instrumentation. Sequence data can be routinely compared to the progenitor wild-type allele. This analysis reveals the extent of diversity of changes conditioning heat stability.

Several of the sequenced HS mutants contained the identical histidine to tyrosine change at amino acid position 333 in the large subunit. PCR-derived HS mutants can be quickly screened for the histidine to tyrosine alteration by use of site-specific mutagenesis using primers that change the tyrosine back to histidine.

EXAMPLE 3

Expression, Purification, and Kinetic Analysis of Genetic Variants

Conditions for the expression of the wild-type maize endosperm AGP in *E. coli* have been fully characterized. Optimum growth and induction conditions vary somewhat from those previously published for potato AGP expressed in *E. coli* (Iglesias et al., 1993, supra; Ballicora et al., 1995, supra). Induction at room temperature for 12-14 hrs in the presence of 0.3 mM IPTG and 25 µg/ml nalidixic acid consistently gives high levels of expression and activity. Addition of 30% ammonium sulfate and 10 mM $KH_2PO_4^-$/$K_2HPO_4^-$ to the extraction buffer stabilizes the maize AGP in the crude extract.

Ammonium sulfate concentrated AGP is further purified by Hydrophobic Interaction Chromatography using Tentacle C3 aminopropyl media (EM Separations) packed into a Pharmacia HR 10/10 column. Protein binds to the column in a buffer containing 1 M ammonium sulfate. AGP is eluted from the column by successive step gradient washes of buffer that contains 0.75 M, 0.5 M, 0.25 M, and 0 M ammonium sulfate. Wild-type maize endosperm AGP typically elutes in the 0.25 M wash. C3 purified maize endosperm AGP is further purified by anion exchange chromatography using Macro-Prep DEAE (BioRad) anion exchange media packed into a Pharmacia HR 10/10 column. AGP is eluted by a linear gradient of 100-500 mM KCl, and typically elutes at a salt concentration around 300 mM. A Pharmacia FPLC system is used for all chromatography steps. The conditions for the individual purification steps are fully characterized. AGP activity during the purification is monitored by the pyrophosphorylysis assay, and purification steps are monitored by SDS-PAGE, Coomassie staining, and Western analysis using polyclonal antibodies specific to the maize endosperm AGP large and small subunits.

EXAMPLE 4

Enhanced Subunit Interaction

A totally unexpected pleiotropic effect of the HS maize endosperm AGP mutants is a two- to three-fold elevation of activity before heat treatment. One possible explanation for this result is that we have, by mutational change, shifted the ratio of SH2 and BT2 monomers and polymers existing within the *E. coli* cell. Perhaps, in wild-type, only 10% or less of the total proteins exist in the active heterotetrameric form whereas in the mutants, this percentage is much higher. If the polymer is more heat resistant than are the monomers, then the phenotype of the mutants would be identical to what has been observed. Kinetic analysis can be used to determine changes in affinities for substrates and/or allosteric effectors.

To test the idea that the monomer/polymer ratio may be altered in these mutants, the amounts of monomers and polymers in wild-type and in selected mutants both before and after heat treatment can be monitored. The availability of antibodies (Giroux, M. J. and Hannah, L. C. [1994] *Mol. Gen. Genetics* 243:400-408) for both subunits makes this approach feasible. This can be examined both through sucrose gradient ultracentrifugation and through gel chromatography and will readily determine which method is most efficient and definitive.

Since the higher plant AGP consists of two similar but distinct subunits that oligomerize to form the native heterotetrameric structure, mutations that enhance this interaction can provide added stability to the enzyme. A yeast two-hybrid system (CLONTECH Laboratories, Palo Alto, Calif.) can be used to evaluate subunit interactions. Specific primers for the amplification of the coding regions can be constructed. These primers add unique restriction sites to the 5'- and 3'-ends so that cloning facilitates the translational fusion of the individual subunit to the GAL4 DNA binding domain (pGBT9) or GAL4 activation domain (pGAD424). If the proteins cloned into the vectors interact, the DNA binding domain and the activation domain will form a functional transcription activator. This in turn activates expression of the reporter gene, lac Z, cloned behind a GAL4 promoter.

Initially, conditions can be characterized with the wild-type subunits. The coding regions of the wild-type large and small subunits can be cloned into the pGBT9 and pGAD424 yeast expression vectors. All possible combinations can be generated and tested. pGBT9 and pGAD424 vectors containing Sh2 and Bt2 can be cotransformed into the same yeast strain, and selected for growth on media lacking tryptophan (pGBT9) and leucine (pGAD424). Subunit interaction as a function of lacZ expression can be detected two ways. Positive colonies are visually identified by a B-galactosidase filter assay. With this assay colonies are bound to the filter, lysed, and incubated with an X-gal solution. Colonies that exhibit a blue color can be analyzed. Subunit interaction can be further analyzed by an enzyme assay specific for B-galactosidase. This allows the quantification of the interaction. Mutations that enhance subunit interactions will give higher levels of B-galactosidase activity when assayed.

EXAMPLE 5

Further Enhancement of Stability

The large subunit mutants isolated vary in their heat stability characteristics, suggesting the possibility of multiple mutations. While sequence analysis of mutants HS 33 and HS 40 reveal that the mutant sequences are not identical, both mutants contained the identical histidine to tyrosine change. Given the identification of different HS alterations within the SH2 protein, it is possible to efficiently pyramid these changes into one protein. Furthermore, any HS mutations within the small subunit can be co-expressed with HS SH2 mutants to further enhance the stability of the maize endosperm enzyme.

Multiple HS mutants within one subunit can easily be combined. For example, different unique restriction sites that divide the coding regions of Sh2 into three distinct fragments can be used. Where appropriate, mutation combinations can be generated by subcloning the corresponding fragment containing the added mutation. If two mutations are in close proximity, then site-directed mutagenesis can be used to engineer such combinations. One method for site specific mutations involves PCR, mutagenic primer, and the use of DpnI restriction endonuclease. Primers can be constructed to contain the mutation in the 5' end, and used to PCR amplify using the proofreading polymerase Vent. Amplified DNA can then be digested with DpnI. Parental DNA isolated from *E. coli* is methylated and hence susceptible to DpnI. Digested DNA is size fractionated by gel electrophoresis, ligated, and cloned into the expression vectors. Mutations are confirmed by sequence analysis and transformed into the AC70R1-504 strain carrying the wild-type small subunit. Combinatorial mutants can then be analyzed.

EXAMPLE 6

Identification of Additional Mutants at Position 333 of the Large Subunit of Maize AGP Hydroxylamine-HCl mutagenesis gives rise only to cytosine to thymine changes, thereby limiting the types of possible substitutions. Because both strands of DNA undergo mutagenesis, thymine to cytosine changes also occur; however, taken together, only two of the 12 possible single base changes occur. Hence, not all possible amino acid substitutions would have been produced by hydroxylamine-HCl mutagenesis.

Therefore, in order to prepare mutants where each of the 20 different amino acids were inserted, individually, at position 333 of the large subunit of maize endosperm AGP, a two step process was employed. Methodologies were derived basically from those of Stratagene. First, the codon encoding amino acid 333, plus the first base of the codon for amino acid 334, were removed via PCR-based site-specific mutagenesis (Suzuki et al., 1989, supra). Following screening for inactivity by iodine staining and subsequent sequencing to verify the deletion, the resulting plasmid was PCR mutagenized using a primer containing randomized bases at the 333 codon plus the replacement base at the first base of the codon for amino acid 334. Resulting plasmids were transformed into Bt2-containing E. coli mutant cells, screened via iodine staining for activity at 37° C. and at 42° C., and subsequently sequenced. Primers of lesser degeneracy were used in latter stages to more efficiently generate codons not obtained in the first round.

All 20 amino acid substitutions were isolated following mutagenesis and all gave rise to staining at 37° C. Mutants were also scored for iodine staining at the elevated temperature of 42° C. Coded strains were used for screening to remove any possible bias on the part of the investigators. Those mutants giving rise to staining equal to or greater than wildtype when grown at 42° C., are listed in Table 3 below.

As expected, the screening identified active enzymes having at position 333 of the protein the wild type amino acid, i.e., histidine, or the amino acid of the HS 33 mutant, i.e., tyrosine. Phenylalanine, which differs from tyrosine only by the absence of a polar hydroxyl group, was also identified. The screen also identified active enzymes having amino acids differing substantially from tyrosine and phenylalanine, such as, for example, glycine.

AGP activities before and after treatment of freshly extracted enzyme preparations at 65° C. for 5 minutes were also measured and results are shown in Table 3. Of the eight amino acids selected through positive staining E. coli plates grown at 42° C., three mutants (HS 33, HS 33F, and HS 33M having tyrosine, phenylalanine, or methionine at position 333, respectively) proved superior activity in enzyme assays following heat treatment at 65° C. While AGP activities from phenylalanine- and methionine-containing AGPs are somewhat higher than that conditioned by the tyrosine substitution, the differences in activity between these three preparations are small.

TABLE 3

| Amino Acid | Before Heat* | After Heat* |
|---|---|---|
| histidine (wt) | 61 | 42 |
| tyrosine (HS 33) | 100 | 77 |
| phenylalanine | 138 | 85 |
| methionine | 160 | 89 |
| cysteine | 73 | 7 |
| lysine | 48 | 38 |
| glycine | 102 | 34 |
| glutamine | 65 | 21 |

*AGP activity in crude preps is expressed as a percentage of HS 33 activity before heat treatment.

EXAMPLE 7

Combination of Heat Stability Mutations with Rev6

According to the subject invention, the heat stable mutations can be combined with a mutation associated with increased seed weight, such as, for example, the Rev6 mutation. The goal is to maintain the desired phosphate insensitivity characteristic of Rev6 while enhancing its stability. Rev 6/HS double mutants can be constructed and confirmed as described herein. Double mutants can be transformed into AC70R1-504 carrying the wild-type small subunit. Increased heat stability can be easily identified by a positive glycogen staining on a low glucose media. Rev6 does not stain when grown on this media. Initially all mutant combinations can be screened enzymatically for maintenance of phosphate insensitivity, and only combinations that maintain phosphate insensitivity are further analyzed.

EXAMPLE 8

Cloning of SSS I Mutants

A glg A⁻ E. coli strain deficient in the endogenous bacterial glycogen synthase can be obtained from the E. coli Stock Center. Bacterial expression vectors currently used for the expression of AGP can be used for expression of SSS.

One cloning strategy, as used, for example, with Sh2 and Bt2 (Giroux et al., 1996, supra), is the following: One primer contains a unique restriction plus the 5' terminus of the transcript while the other primer contains another unique restriction site and sequences 3' to the translational termination codon of the gene under investigation. Subsequent cloning of these gives rise to a translational fusion within the plasmid. These gene specific primers are initially used in RT-PCR reactions using poly A+RNA from developing endosperms.

Expression of the maize endosperm SSS I will complement the lack of glycogen synthase activity in the glg A⁻ strain. Complementation should be easily visualized with iodine staining as it is with the expression of AGP in the glg C⁻ strain. Crude extracts can be incubated at various temperatures and lengths of time to determine the heat stability of SSS I. The glg A⁻ strain expressing the maize endosperm SSS I can be grown at various temperatures to determine if function is temperature sensitive as it is with the AGP bacterial expression system. Once a restrictive temperature is established, a random mutagenesis can be conducted with the SSS I clone. Mutant forms of SSS I can be transformed into the glg A⁻ strain, grown at the restrictive temperature, and heat stable variants identified by their ability to produce iodine-staining glycogen at the restriction temperature.

EXAMPLE 9

Temperature Sensitive Mutants of Maize Endosperm ADP-Glucose Pyrophosphorylase

As an alternative approach to identify additional variants with increased stability, a reverse-genetics approach was employed. Temperature sensitive (TS) mutants have been isolated. These mutants exhibit a negative iodine staining phenotype at 30° C. indicating a lack of function with the maize endosperm AGP. In contrast, when the mutants are grown at 37° C. they can fully complement the mutation in the bacterial AGP. This clearly shows that the mutant AGPs are functional, and that the loss of function is temperature dependent. Wild type AGP exhibits a positive glycogen staining phenotype at 30° and 37° C. The temperature sensitive mutants were then used to produce second site revertants that encode mutant AGP having enhanced stability.

Mutagenesis. pSh2 DNA was subjected to hydroxylamine mutagenesis (Greene, T. W., Chantler, S. E., Kahn, M. L., Barry, G. F., Preiss, J., and Okita, T. W. [1996] *Proc. Natl. Acad. Sci.* 93:1509-1513) and transformed into AC70R1-504 *E. coli* cells carrying the wild type pBt2 small subunit plasmid. Cells were plated and grown at 30° C. Temperature sensitive variants of AGP were identified by their negative iodine staining phenotype at 30° C. Putative mutants were streaked again at 30° C. and 37° C. along with the wild type AGP as a control. Six mutants that consistently gave a negative iodine phenotype at 30° C. and a positive iodine staining phenotype at 37° C. were isolated. Expression of wild type Sh2 and Bt2 gave a positive iodine staining phenotype at both temperatures.

Characterization of TS48 and TS60. Plasmid DNA from two temperature sensitive mutants, TS48 and TS60, was isolated and sequenced to identify the genetic lesion. A single point mutation that generated the replacement of leucine at amino acid position 426 with phenylalanine was identified (FIG. 4A). This residue and surrounding region is highly conserved in the cereal endosperm large subunits (LS) (Smith-White and Preiss, 1992, supra). In TS60, two point mutations were identified that generated a glutamic acid to lysine change at amino acid 324 and an alanine to valine mutation at position 359 (FIG. 4B). Glu-324 is highly conserved among the LS and small (SS) subunits of AGP (Smith-White and Preiss, 1992, supra). Ala-359 and the surrounding amino acids are also highly conserved among the AGP LS. Of significance, the two mutation identified in TS60 flank the HS 33 mutation described herein. The HS 33 mutation, which has the histidine to tyrosine substitution at position 333, was shown to greatly enhance heat stability of the maize endosperm AGP. That the mutations of TS60 are in close proximity to the HS 33 mutation is additional evidence that this region of the protein is important for stability.

Isolation of second-site revertants. Isolation of the temperature sensitive mutants provides a selectable phenotype for isolating additional variants that enhance the stability of AGP. Additional hydroxylamine mutagenesis was conducted with TS48 and TS60 DNA to isolate second-site revertants that restore a positive glycogen staining phenotype at 30° C. Hydroxylamine was used because the chemistry of the mutagenesis eliminates the possibility of a direct reversion of the primary mutation identified in the TS48 and TS60 mutants. This forces the selection of second-site mutations that can restore stability in these temperature sensitive mutants.

Three revertants were isolated for TS48 and the molecular characterization of one mutant, RTS 48-2, is shown (FIG. 5A). RTS 48-2 contains an alanine to valine mutation at amino acid position 177 in addition to the parental mutation identified in TS48. This residue and the surrounding region are highly conserved. The RTS 48-2 mutation corresponds to the identical site of the mutation identified in the heat stable mutant, HS 13. The alanine residue was mutated to a proline at position 177 in HS 13. That these two mutations map to the same site is significant. The RTS 48-2 and HS 13 mutants were selected based on increased stability using completely different approaches, and thus these two mutations identify this site to be important in the stability of AGP.

Five second-site revertants were isolated for TS60 and the sequence analysis of one, RTS 60-1, is shown (FIG. 5B). An alanine to valine mutation at amino acid 396 was identified. This residue is highly conserved among the AGP LS, and it also maps close to a heat stable mutation identified in HS 14.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated polynucleotide comprising a nucleotide sequence encoding a mutant large subunit of a plant ADP-glucose pyrophosphorylase (AGP) protein, or a biologically-active fragment of said mutant protein, wherein when said mutant large subunit protein is expressed to form a mutant ADP-glucose pyrophosphorylase enzyme, said mutant enzyme, or a biologically-active fragment of said mutant enzyme, exhibits increased heat stability relative to wild type ADP-glucose pyrophosphorylase enzyme, and wherein said mutant large subunit protein encoded by said polynucleotide comprises an amino acid mutation wherein the amino acid corresponding to the histidine at position 333 in the amino acid sequence of a wild type large subunit of ADP-glucose pyrophosphorylase polypeptide of maize is replaced by an amino acid that confers said increased heat stability on said mutant enzyme.

2. The polynucleotide according to claim 1, wherein said amino acid corresponding to said histidine at position 333 is replaced by a glycine.

3. The polynucleotide according to claim 1, wherein said amino acid corresponding to said histidine at position 333 is replaced by a phenylalanine.

4. The polynucleotide according to claim 1, wherein said amino acid corresponding to said histidine at position 333 is replaced by a methionine.

5. The polynucleotide according to claim 1, wherein said mutant large subunit protein encoded by said polynucleotide further comprises an amino acid mutation that confers increased seed weight to a plant expressing said polynucleotide.

6. The polynucleotide according to claim 5, wherein said polynucleotide comprises the Rev6 mutation.

7. The polynucleotide according to claim 5, wherein said polynucleotide encodes a maize large subunit AGP enzyme wherein at least one serine residue is inserted between amino acids 494 and 495 of a wild type AGP enzyme large subunit.

8. The polynucleotide according to claim 5, wherein said polynucleotide encodes a maize large subunit AGP enzyme wherein the amino acid pair tyrosine:serine is inserted between amino acids 494 and 495 of the wild type AGP enzyme subunit or said polynucleotide encodes a maize large subunit AGP enzyme wherein the amino acid pair serine:tyrosine is inserted between amino acids 495 and 496 of a wild type AGP enzyme large subunit.

9. A method for increasing resistance of a plant to heat stress conditions, said method comprising incorporating a polynucleotide comprising a nucleotide sequence encoding a mutant large subunit of a plant ADP-glucose pyrophosphorylase (AGP) protein, or a biologically-active fragment of said mutant protein, wherein when said mutant large subunit protein is expressed to form a mutant ADP-glucose pyrophosphorylase enzyme, said mutant enzyme, or a biologically-active fragment of said mutant enzyme, exhibits increased heat stability relative to wild type ADP-glucose pyrophosphorylase enzyme, and wherein said mutant large subunit protein encoded by said polynucleotide comprises an amino acid mutation wherein the amino acid corresponding to the histidine at position 333 in the amino acid sequence of a wild type large subunit of ADP-glucose pyrophosphorylase polypeptide of maize is replaced by an amino acid that confers said increased heat stability on said mutant enzyme into the genome of said plant and expressing the protein encoded by said polynucleotide molecule.

10. The method according to claim 9, wherein said plant is a monocotyledonous plant.

11. The method according to claim 10, wherein said monocotyledonous plant is selected from the group consisting of rice, wheat, barley, oats, sorghum, maize, lilies, and millet.

12. The method according to claim 9, wherein said plant is Zea mays.

13. The method according to claim 9, wherein said plant is a dicotyledonous plant.

14. A plant, plant tissue, or plant seed comprising a polynucleotide comprising a nucleotide sequence encoding a mutant large subunit of a plant ADP-glucose pyrophosphorylase (AGP) protein, or a biologically-active fragment of said mutant protein, wherein when said mutant large subunit protein is expressed to form a mutant ADP-glucose pyrophosphorylase enzyme, said mutant enzyme, or a biologically-active fragment of said mutant enzyme, exhibits increased heat stability relative to wild type ADP-glucose pyrophosphorylase enzyme, and wherein said mutant large subunit protein encoded by said polynucleotide comprises an amino acid mutation wherein the amino acid corresponding to the histidine at position 333 in the amino acid sequence of a wild type large subunit of ADP-glucose pyrophosphorylase polypeptide of maize is replaced by an amino acid that confers said increased heat stability on said mutant enzyme.

15. The plant, plant tissue, or plant seed according to claim 14, wherein said plant, plant tissue, or plant seed is monocotyledonous.

16. The plant, plant tissue, or plant seed according to claim 15, wherein said monocotyledonous plant, plant tissue, or plant seed is selected from the group consisting of rice, wheat, barley, oats, sorghum, maize, lilies, and millet.

17. The plant, plant tissue, or plant seed according to claim 14, wherein said plant is Zea mays or said plant tissue or plant seed is from Zea mays.

18. The plant, plant tissue, or plant seed according to claim 14, wherein said plant, plant tissue, or plant seed is dicotyledonous.

19. The polynucleotide according to claim 2, wherein said mutant protein encoded by said polynucleotide comprises the amino acid sequence shown in SEQ ID NO. 37.

20. The polynucleotide according to claim 3, wherein said mutant protein encoded by said polynucleotide comprises the amino acid sequence shown in SEQ ID NO. 38.

21. The polynucleotide according to claim 4, wherein said mutant protein encoded by said polynucleotide comprises the amino acid sequence shown in SEQ ID NO. 39.

* * * * *